(12) United States Patent
Wilson et al.

(10) Patent No.: US 9,242,077 B2
(45) Date of Patent: Jan. 26, 2016

(54) DYNAMIC ADJUSTMENT TOOL FOR PROGRAMMING AN IMPLANTABLE VALVE

(71) Applicant: DePuy Synthes Products, LLC, Raynham, MA (US)

(72) Inventors: Stephen Wilson, North Easton, MA (US); Alyssa Trigger, South Boston, MA (US); Brian Soares, Norton, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 333 days.

(21) Appl. No.: 13/795,139

(22) Filed: Mar. 12, 2013

(65) Prior Publication Data

US 2014/0276339 A1 Sep. 18, 2014

(51) Int. Cl.
F16K 37/00 (2006.01)
F16K 31/08 (2006.01)
A61M 27/00 (2006.01)

(52) U.S. Cl.
CPC ............. *A61M 27/006* (2013.01); *F16K 31/08* (2013.01); *F16K 31/088* (2013.01); *F16K 37/0041* (2013.01); *A61M 2205/3515* (2013.01); *A61M 2205/8287* (2013.01); *Y10T 137/8225* (2015.04); *Y10T 137/8242* (2015.04)

(58) Field of Classification Search
CPC .................. A61M 27/006; A61M 2205/3515; A61M 2205/8287; F16K 31/088; F16K 37/0041; Y10T 137/8242; Y10T 137/8225
USPC ............ 604/9, 891; 251/65, 129.06; 137/553, 137/554
See application file for complete search history.

(56) References Cited

U.S. PATENT DOCUMENTS

| | | | |
|---|---|---|---|
| 4,540,400 A * | 9/1985 | Hooven | 604/9 |
| 5,643,194 A | 7/1997 | Negre | |
| 7,921,571 B2 | 4/2011 | Moureaux et al. | |
| 8,038,641 B2 | 10/2011 | Soares et al. | |
| 8,241,240 B2 | 8/2012 | Murphy | |
| 2002/0022793 A1 | 2/2002 | Bertrand et al. | |
| 2005/0022403 A1 | 2/2005 | Moskowitz et al. | |
| 2005/0120571 A1 | 6/2005 | Moskowitz et al. | |

(Continued)

FOREIGN PATENT DOCUMENTS

| | | |
|---|---|---|
| EP | 2316520 A1 | 5/2011 |
| EP | 2316522 A1 | 5/2011 |
| FR | 2858239 A1 | 4/2005 |

OTHER PUBLICATIONS

European Search Report dated Oct. 10, 2014.

*Primary Examiner* — Atif Chaudry
(74) *Attorney, Agent, or Firm* — Troutman Sanders LLP

(57) ABSTRACT

A tool includes a locator having a center aligned with a rotor axis when disposed over the valve. The locator has a first dimension approximately perpendicular with the rotor axis. A wall of the locator forms a volume to allow an adjustor to be disposed therein. The adjustor fits within the wall and has a magnet having a magnetic axis to unlock the rotor. An adjustable outer wall has a first position dimension permitting the adjustor to rotate about the center of the locator and aligning the magnetic axis with the center. The adjustable outer wall has a second position dimension less than the first dimension and the first position dimension. The adjustor can move lateral, rotational, and orbital in the locator misaligning the magnetic axis with the center. Misaligning the magnetic and rotor axes unlocks the rotors and the magnet maintains the unlocked state even when the axes are misaligned.

15 Claims, 11 Drawing Sheets

(56) References Cited

U.S. PATENT DOCUMENTS

| | | |
|---|---|---|
| 2011/0048539 A1 | 3/2011 | Negre et al. |
| 2011/0105991 A1 | 5/2011 | Roth et al. |
| 2011/0105992 A1 | 5/2011 | Girardin et al. |
| 2011/0105993 A1 | 5/2011 | Girardin et al. |
| 2011/0105994 A1 | 5/2011 | Ginggen et al. |
| 2014/0121586 A1 | 5/2014 | Bertrand et al. |

* cited by examiner

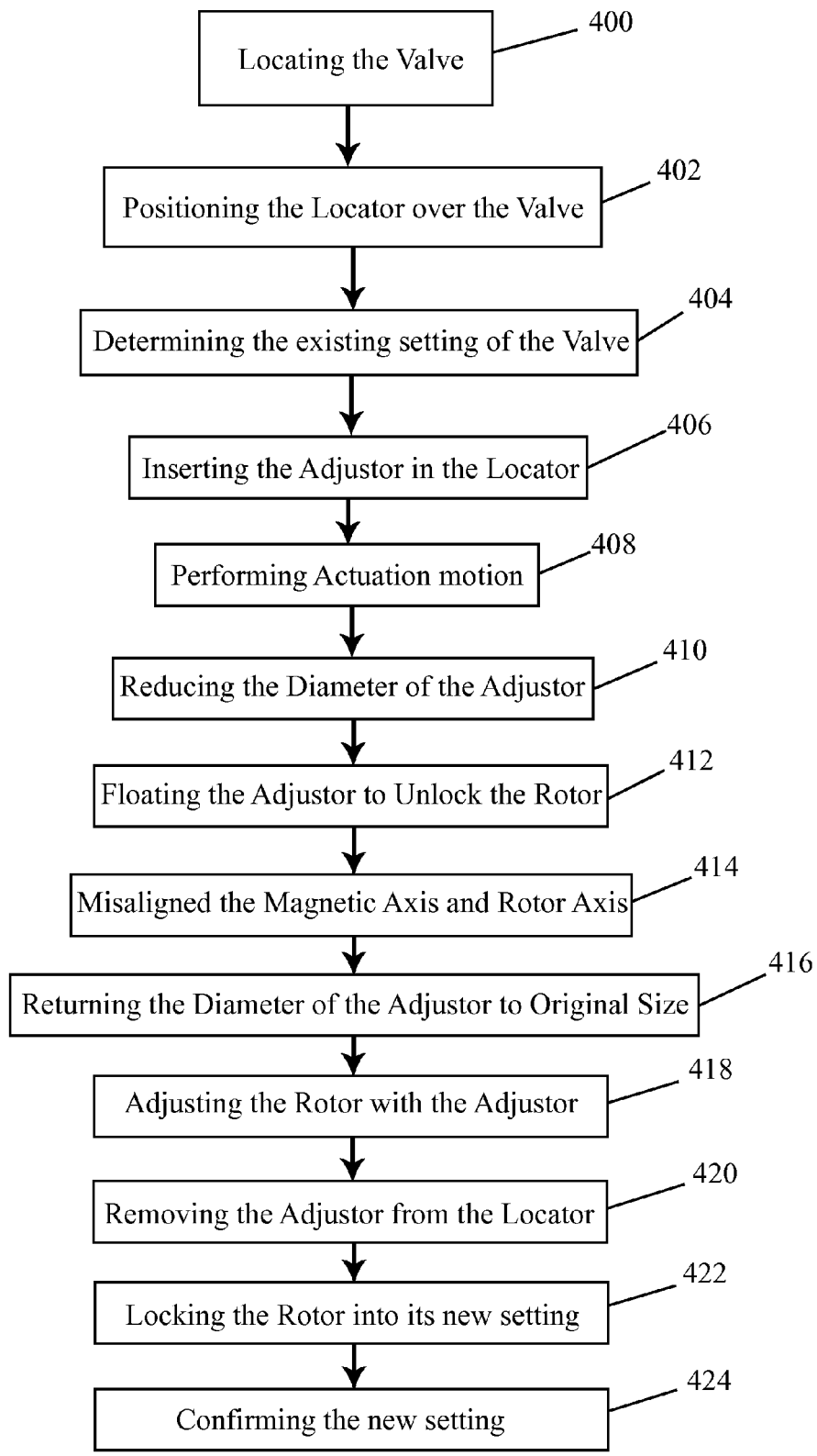

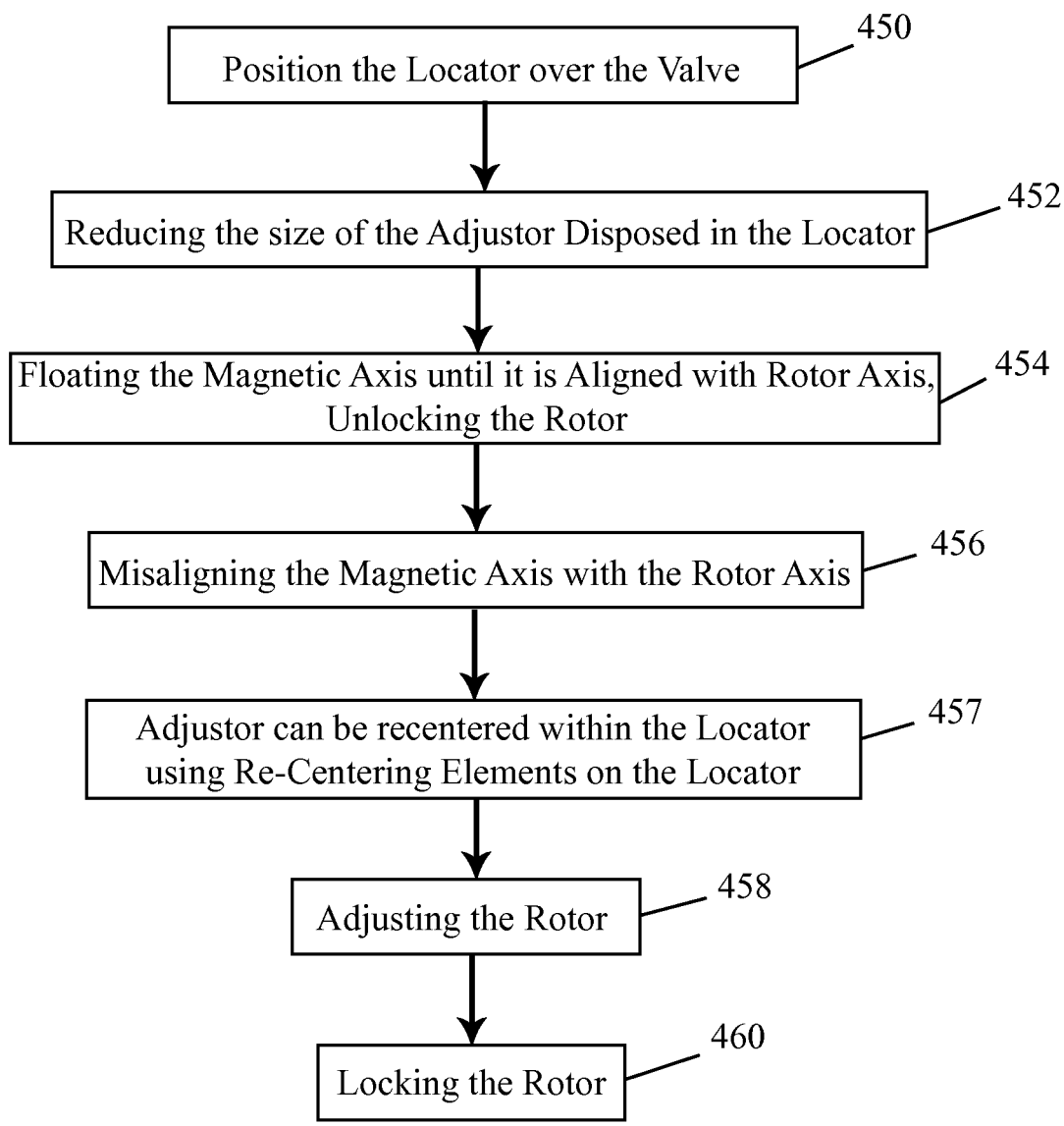

DYNAMIC ADJUSTMENT TOOL FOR PROGRAMMING AN IMPLANTABLE VALVE

FIELD OF THE INVENTION

The invention relates generally to surgically implantable fluid drainage systems. More specifically, the invention relates to extracorporeal tools for setting adjustable valves used for cerebrospinal fluid drainage.

BACKGROUND

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream. Typically, the shunt valve is palpatable by the physician through the patient's skin after implantation.

Shunt valves, which can have a variety of configurations, can be designed to allow adjustment of their fluid drainage characteristics after implantation. It is generally preferred to enable external adjustment of the pressure threshold to avoid invasive surgical procedures each time an adjustment is required. In some shunt systems, the shunt valve contains a magnetized rotor to control the pressure threshold of the valve. Physicians can then use an external adjustment mechanism, such as a magnetic programmer containing a powerful magnet, to adjust the pressure threshold of the shunt valve. One issue with magnetically programmable valves is a potential for unintentionally adjusting the valve by the misapplication of an external magnetic field. Unintentional adjustment of the valve could lead to either the overdrainage or underdrainage of CSF, which can result in dangerous conditions, such as subdural hematoma. For example, the direction of physical approach to the valve by a magnetic programmer, or an inappropriate initial rotational orientation of a magnetic programmer with respect to the valve, has the potential to inadvertently change a setting of the valve.

It is also important to be able to externally read or verify the setting of the valve. With some adjustable valves, x-ray images are used to determine the current setting of the valve, before and after adjustment. With other adjustable valves, the orientation of the rotor in the valve can be read magnetically, using a magnetic compass-like device positioned above the valve, outside the skin of the patient.

Although tools and methods exist for adjusting CSF shunt valve settings, as do other tools and methods for reading a valve setting, some are difficult to get the magnetic axis of the adjustment tool to align with the magnetic axis of the rotor of the valve. If the axes are not aligned, the rotor cannot be set in the adjusting position. Unfortunately, there is no way for the user to determine if the valve's rotors are in the adjusting position. Thus, the user believes that the valve's rotors are in the adjusting position, makes the adjustment, and then on checking the setting, finds that the adjustment was not made. The user may repeat this process numerous times, each time attempting to align the axes to then find the adjustment was not made.

Thus, a need exists for a magnetically programmable valve systems having reduced probability of unintentional adjustment, as well as a tool and method that allows for ease of aligning the magnetic and rotor axes necessary to allow adjustment of an implantable valve's settings.

SUMMARY

Accordingly, the present invention provides tools and methods for externally changing a setting of a magnetically adjustable, implantable valve. An example of a tool for changing a current setting of a magnetically readable and settable valve implanted in a living being is described below. The valve has an internal rotor rotatable about a rotor axis having a locked and an unlocked state. The tool includes a locator having a center aligned with the rotor axis when the locator is disposed over the valve. In this example, the locator can have a bottom with a cut-out of the valve or can be a ring. The locator can also have a first dimension approximately perpendicular with the rotor axis. The first dimension can be a diameter of the locator. A wall of the locator can have a second dimension approximately perpendicular to the first dimension. The wall can form a volume in that the locator has a depth to allow an adjustor to be disposed therein.

The adjustor has an adjustable outer wall that fits at least partially within the wall of the ring. The adjustor has at least one magnet having a magnetic axis. The magnet has a strong enough magnetic field to unlock the internal rotor of the valve. In one example, the magnet is disposed approximately in a center of the adjustable outer wall. The adjustable outer wall has a first position dimension approximately equal to or less than the first dimension of the locator. This sizing permits the adjustor to rotate about the center of the locator. In an example, the only movement of the adjustor permitted within the locator is rotational about the center, accounting for a small amount of play typical between separately formed parts.

The magnetic axis can align with the center of the locator when the adjustor is disposed within and the adjustable outer wall has the first position dimension. The adjustable outer wall also has a second position dimension less than the first dimension and less than the first position dimension. This sizing permits the adjustor to move more freely inside the locator. The adjustor can move at least lateral, rotational, and orbital in the locator. This movement can misalign the magnetic axis with the center of the locator when the adjustor is disposed within and the adjustable outer wall has the second position dimension. When the magnetic axis aligns with the rotor axis, the rotor moves into the unlocked state and the rotation of the adjustor can set the valve when unlocked. The rotor can return to the locked state once the adjustor is removed from the locator. Once the magnet unlocks the rotor, the magnet maintains the rotor in the unlocked state even when the magnetic axis and rotor axis are misaligned.

A plurality of indicators can be disposed on the wall indicating one or more valve settings. In one example, the indicators can be notches or lines on the locator or tabs extending from the wall.

A flexible element can bias the adjustable outer wall to one of the first position dimension or the second position dimension. Thus, the adjustor can be in either position in its static state. The flexible element can be compressed or expanded to allow the adjustable outer wall to move between position dimensions and then move back to its static state. The flexible element can be locked in place or held under force by the user to achieve the non-static position.

All of the above dimension can be diameters.

A method for adjusting the magnetically adjustable valve from a current setting to a target setting is described below. The method can include positioning a locator over the valve and disposing the adjustor at least partially within the locator. Then, permitting the adjustor to move at least two of lateral, rotational, and orbital within the locator. This can include the step of reducing a dimension of the adjustor to less than a comparable dimension of the locator. In other words, reducing the diameter of the adjustor in comparison to the diameter of the locator, the above movement allows the adjustor to be non-concentric with the locator. During the movement of the adjustor, aligning the magnetic axis with the rotor axis displaces the rotor into the unlocked state. When the magnetic axis and the rotor axis are misaligned, the magnet still maintains the unlocked state. The misalignment of the magnetic axis and the rotor axis can occur due to a misalignment of the locator over the valve. This misalignment occurs when the user cannot place the locator in the precise position to align the two axes. Then, the user can adjust the valve to the target setting. Adjusting the valve can include expanding the dimension of the adjustor to permit the adjustor to rotate within the locator. The valve can then be locked again by placing the valve rotor in the locked state by removing the adjustor from the locator. Further, the adjustor can be biased to maintain one of the reduced dimension or the expanded dimension.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

The drawing figures depict one or more implementations in accord with the present teachings, by way of example only, not by way of limitation. In the figures, like reference numerals refer to the same or similar elements.

FIG. 6 is flow chart illustrating an example of a method of adjusting an implanted valve;

FIG. 7 is flow chart illustrating another example of a method of adjusting an implanted valve;

DETAILED DESCRIPTION

Figure 1A:
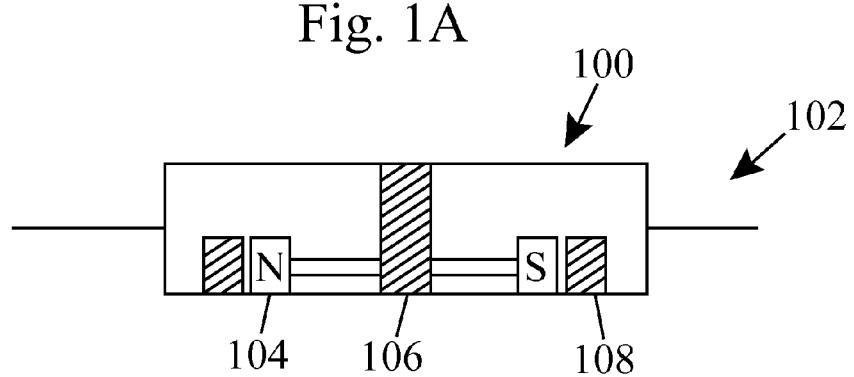
FIG. 1A is a cross-section along line I-I of FIG. 1B illustrating an example of the valve in the locked rotor position.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

Methods and integrated tools of the present invention enable a physician to consistently and reliably change a setting of (adjust) an implantable, magnetically settable valve (valve) from a current setting to a target setting using a dynamic adjustment tool. In an example, the valve is used to control, via its setting, at least one of CSF drainage flow and pressure for a patient with hydrocephalus, is implanted under a patient's scalp or another portion of the patient's skin, and is adjustable from outside (above) the patient's skin.

Other tools and methods for extracorporeally reading and adjusting a hydrocephalus valve are disclosed in U.S. Pat. No. 8,038,641 entitled "Tools and Methods for Programming an Implantable Valve", which is hereby incorporated by reference in its entirety. Within the scope of the present invention, features of the various examples disclosed herein can be used in any combination to construct additional integrated tools and methods for reading and adjusting an implantable valve.

Hydrocephalus valves read and adjusted by tools and methods of the present invention include a magnetic rotor, the rotational orientation of which about a rotor axis is indicative of, and used to modify, the current setting of the valve. An externally applied magnetic field can be used to rotate the rotor about the rotor axis to adjust the valve to the target setting. Additionally, some hydrocephalus valves include a locking element to prevent accidental adjusting of the valve by stray magnetic fields, requiring that a magnetic field for adjusting the valve be applied along the rotor axis to unlock the valve before turning the rotor about the rotor axis.

Any noninvasive means for applying a magnetic field for adjusting the valve, or for sensing the orientation of the rotor to read the valve, can be incorporated in tools and methods of the present invention. In some embodiments, the externally applied magnetic field for adjusting the valve is provided using one or more permanent magnet that can be physically oriented about the rotor axis. In other embodiments, the externally applied magnetic field for adjusting the valve is provided using one or more electromagnet having a magnetic field that can be electronically or physically oriented about the rotor axis.

Reading the current valve setting is accomplished by sensing the rotational orientation of the magnetic rotor about the rotor axis. In some embodiments, sensing the rotational orientation is accomplished using a magnetically responsive mechanical device such as a magnetic compass. In other embodiments, sensing the rotational orientation is accomplished using one or more electronic sensors capable of measuring a magnetic field.

Figure 1B:
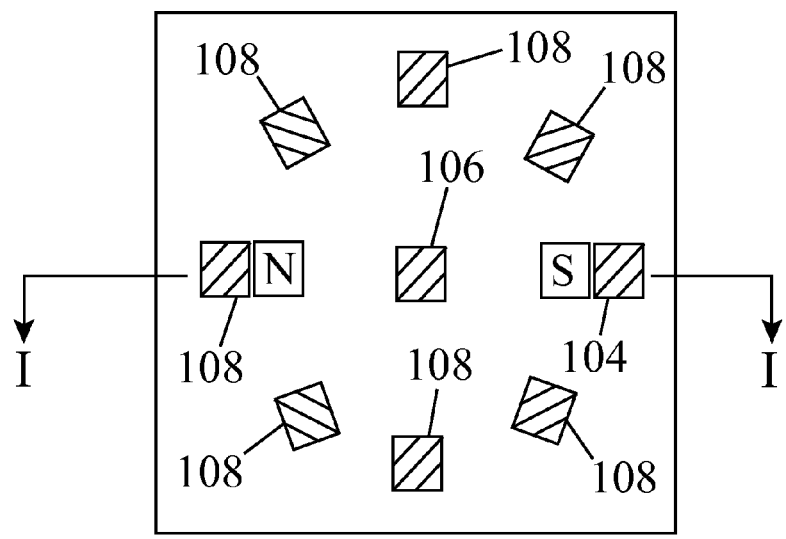
FIG. 1B is a top view of the valve.
Figure 1C:
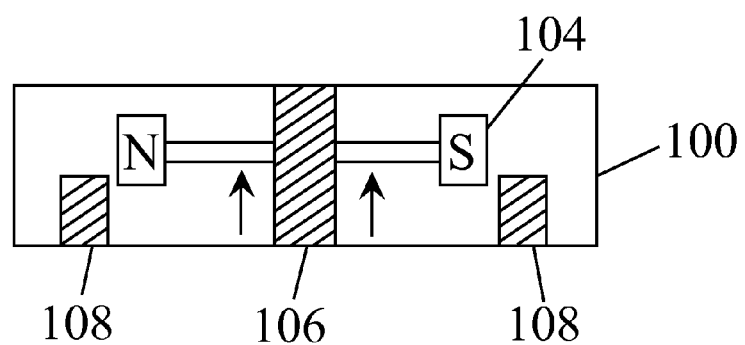
FIG. 1C is a cross-section view along line I-I of FIG. 1B illustrating the valve in the unlocked rotor position.

FIGS. 1A, 1B, and 1C illustrate a generalized implantable valve 100 implanted beneath a patient's skin 102. The valve 100 includes a magnetic rotor 104 having a rotor axis 106 about which the rotor 104 can be rotated by application of a magnetic field, to adjust the valve 100. In an example, the valve 100 has a plurality of predetermined settings corresponding to a plurality of predetermined rotational orientations of the rotor 104 about the rotor axis 106. In an example, the plurality of settings comprises eight settings.

It is to be understood that the valve 100 can be any magnetically settable, implantable valve comprising a magnetically rotatable rotor, and further including valves that can be magnetically unlocked. In an embodiment, the valve 100 is unlocked for rotation about the rotor axis 106 by a displacement of the rotor 104 along the rotor axis 106, the displacement provided by application an attractive magnetic field along the rotor axis 106. In a further embodiment, the attractive magnetic field and the magnetic field for rotating the rotor about the rotor axis are provided by a single magnetic source that can be either a permanent magnet or an electromagnet.

FIG. 1A is a cross-section of the valve 100 when the rotor 104 is in the locked position. The rotor 104 is set in a locking element 108. The locking element 108 is configured to prevent the rotor 104 from rotating around the rotor axis 106 to an alternative setting. Note, that in some examples, the rotor 104 can rotate within the valve 100 while locked. FIG. 1B illustrates that the locking element 108 is spaced around the rotor axis 106 to allow for the predetermined rotational orientations of the rotor 104 about the rotor axis 106. The predetermined rotational orientations of the rotor 104 correspond to flow and pressure settings of the valve 100. For example, the valve 100 can be set to flow rates between 5-50 ml/hr to maintain pressures between 0-500 mm $H_2O$, between eight distinct settings. FIG. 1C is the same cross-section as FIG. 1A, except for the fact that the rotor 104 has been displaced along the rotor axis 106. This displacement removes the rotor 104 from the locking element 108 and the rotor 104 is now free to rotate around the rotor axis 106. Once rotated about the rotor axis 106 to a new position, the rotor 104 can be set back within the locking element 108 to lock the rotor 104 such that it is confined in the new position.

Figure 2A:
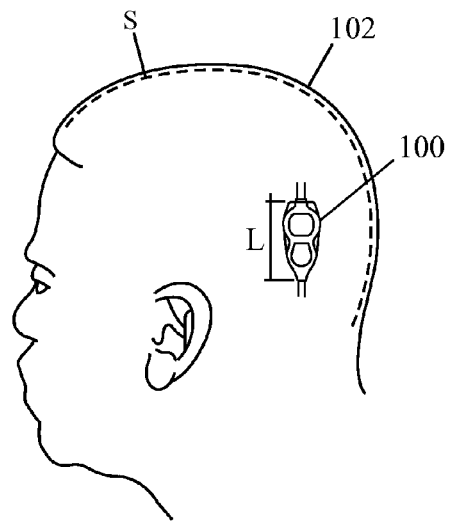
FIG. 2A is an illustration of the valve implanted in a patient.

FIG. 2A illustrates the valve 100 implanted under the skin 102 of a patient's skull S. Once implanted, the valve is under the skin and typically covered by hair. Additionally, the area surrounding the valve may experience localized swelling, especially after surgery. To locate the valve 100 under the skin 102, the user typically palpates the skin 102 until she can feel the valve 100. In one example, to facilitate the adjustment of the valve, a locator 200 is placed over the valve 100 on top of the skin 102 of the skull S.

Figure 2B:
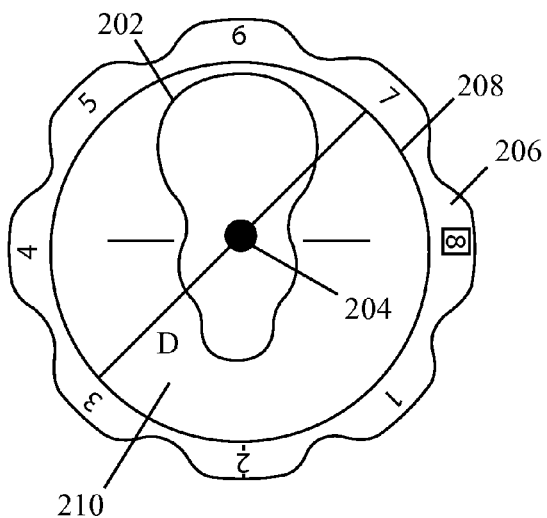
FIG. 2B is a top view of an example of a locator.

FIG. 2B illustrates an example of the locator 200. The locator 200 can be typically circular and can have a diameter D larger than a length L of the valve 100. The locator 200 can have a cut-out 202 or gap shaped similar to the valve 100. This allows the locator 200 to be oriented in the proper direction when placed over the valve 100. The cut-out 202 can be oriented such that once placed over the valve 100 the rotor axis 106 is aligned with a center 204 of the locator 200. While an example can be circular, the locator 200 can have any shape to allow the rotation and translation movements described below. Thus, in one example, the locator 200 can be non-circular and composed of numerous line segments.

Figure 2C:
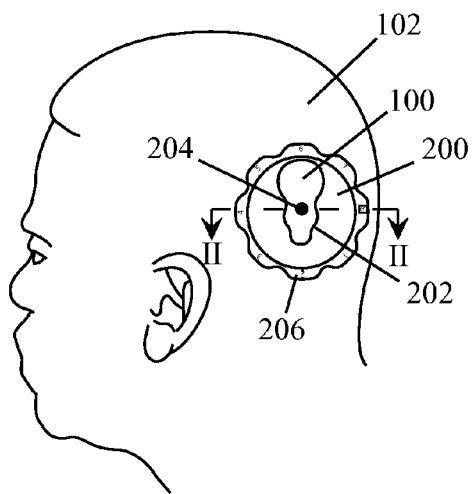
FIG. 2C is an illustration of the valve and locator as used on a patient.

The locator 200 can also have indicators 206, these can be petals or tabs extending outside a circumference 208 defined by the diameter D (wherein circumference 208 equals 2×diameter D). FIG. 2C illustrates a top view of the locator 200 placed over the valve 100 on the patient's skull S.

Figure 2D:
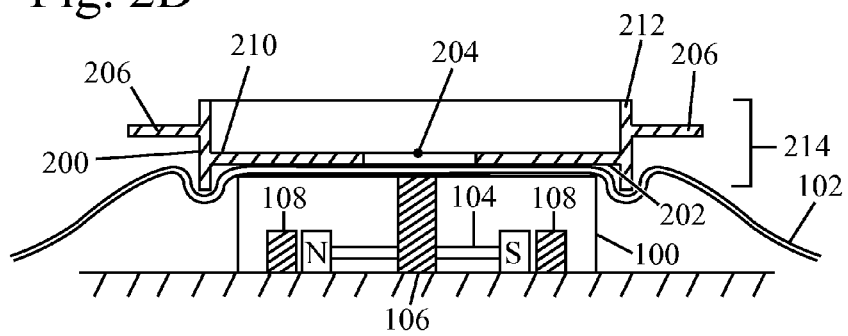
FIG. 2D is a cross-sectional view along line II-II of FIG. 2C illustrating the valve and locator in use.

FIG. 2D is a cross section illustrating both the valve 100 and the locator 200. The cut-out 202 of the locator 200 can be placed over the valve 100 and can even receive a small portion of the valve 100, as the skin 102 may allow. The cut-out 202 can be formed in a bottom 210 of the locator 200. The locator 200 also can have a circumferential wall 212 depending from the bottom 210 and, in one example, encircling the entire bottom 210. The indicators 206 can depend from the circumferential wall 212 and a height 214 of the circumferential wall 212 can form a space or volume, within the locator 200.

Figure 3A:
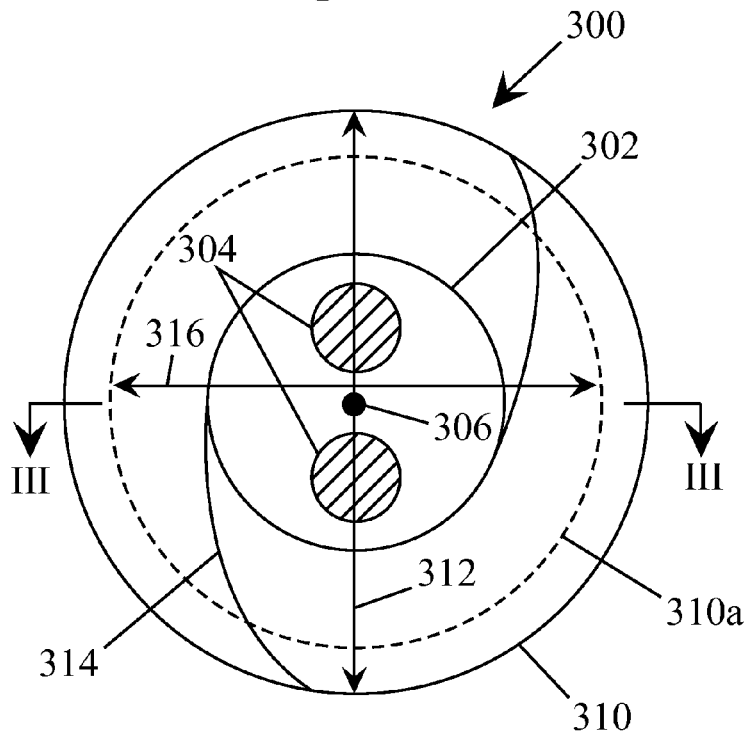
FIG. 3A is a top cross-sectional view of an example of an adjustor.
Figure 3B:
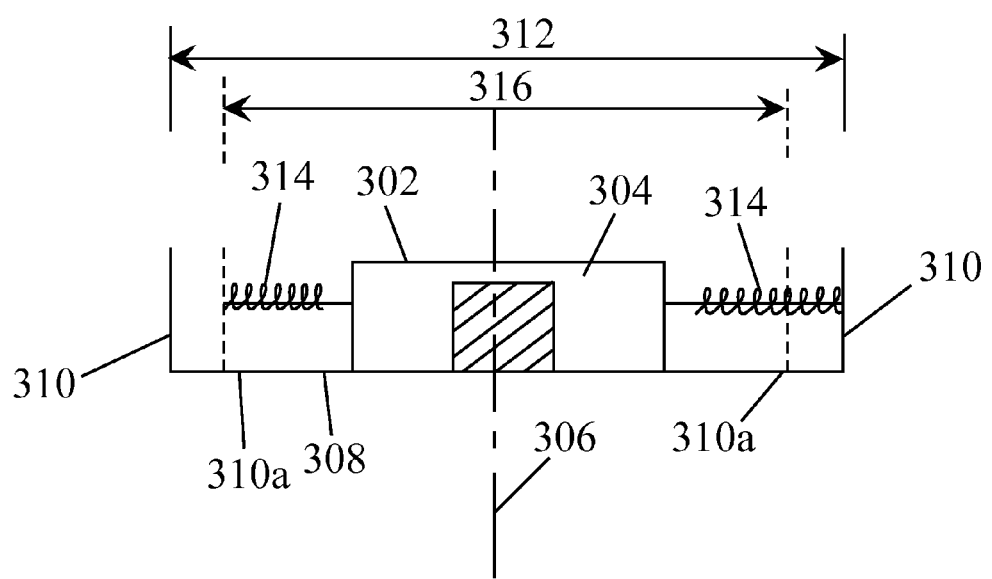
FIG. 3B is a cross-sectional view along line III-III of FIG. 3A illustrating the adjustor.

Turning now to FIGS. 3A and 3B, an example of an adjustor 300 is illustrated. The adjustor 300 is sectioned to see within, and can have a magnetic core 302 including one or more magnets 304 fixed inside the core 302. As above, the magnets 304 can be permanent or electromagnets. In one example, the core 302 can be centered inside the adjustor 300. The magnets 304 can form a magnetic axis 306 which can also be centered inside the core 302 and the adjustor 300. The magnetic axis 306 can be the intersection point of the magnetic fields of the magnets 304, where the magnetic force of the adjustor 300 coupling to the magnetic rotor 104 is the strongest. The adjustor 300 can also have a bottom 308 and a wall 310 extending from the bottom 308 to form a cavity for the core 302. The wall 310 can be a circular perimeter of the adjustor 300 or can be formed from two or more segments. The wall 310 can be held in place at a first wall diameter 312 by one or more resilient elements, (e.g. springs) 314. Upon an actuation motion, which in some examples can be a rotational, twisting, or compressive motion, the springs 314 are compressed or flexed and the wall 310 is drawn toward the core to a second wall position 310a. The second wall position 310a provides a second wall diameter 316. The second wall diameter 316 can be smaller than the first wall diameter 312. Once the actuation motion is released, the springs 314 can be released and the wall can return to the position of the first wall diameter 312. Note, that in one example, the core 302 does not change its position within the adjustor, only the wall 310 changes it relative position.

The resilient elements 314, as described above, can be used to re-center the adjustor 300 within the locator 200. Re-centering, in one example, results in the magnetic axis 306 and the center 204 of the locator 200 being coaxial. However, other elements (not illustrated) within the locator 200 and adjustor 300 that assist in providing some tactile feedback when rotating the adjustor 300 within the locator 200 can also be used to re-center the adjustor 300, for example, detent balls and cam mechanisms.

Figure 3C:
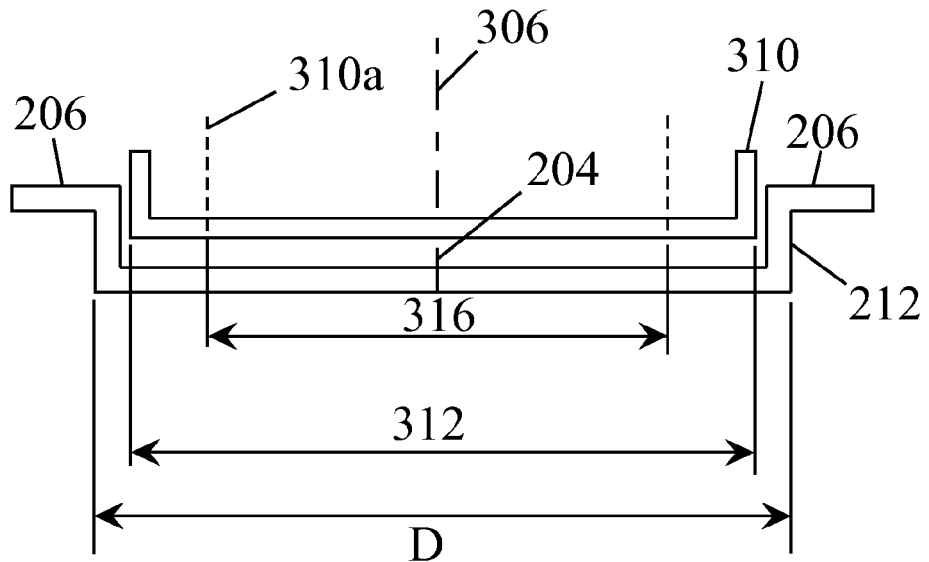
FIG. 3C is a cross-section of an example the adjustor inside the locator.

As illustrated in FIG. 3C, the first wall diameter 312 is approximately equal to the diameter D of the locator 200, and in one example, smaller. In this way, the adjustor 300 can fit within and rotate inside a portion of the locator 200. In one example, the bottom of the adjustor 308 can be in contact with the bottom of the locator 210. When the adjustor 300 is at the first wall diameter 312 position, there can be little or no gap between the adjustor wall 310 and the circumferential wall 212 of the locator 200. This fit between the two walls 212, 310 can prevent most or all lateral or orbital movement of the adjustor 300 within the locator 200. In an example, the only movement permitted when the wall 310 is at the first wall diameter 312 is rotational movement within the locator 200 about the center 204. This example allows the adjustor 300 to rotate between indicators 206. In the first wall diameter 312 position, the magnetic axis 306 can be aligned, or coaxial, with the center 204 of the locator 200.

Once an actuation motion is applied to the adjustor 300 and the wall is in the second wall position 310a, the second wall diameter 316 is also less than the diameter D of the locator 200.

In an example:
the first wall diameter 312≤D and the second wall diameter 316<<D.

Figure 3D:
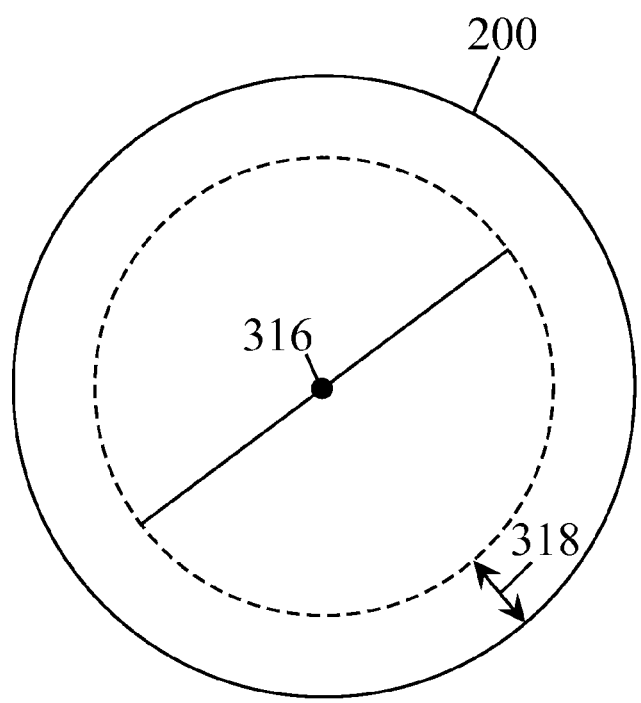
FIG. 3D is a top view of an example of the adjustor in the second wall diameter position inside the adjustor.

Alternately:
the second wall diameter 316<first wall diameter 312≤D. This reduction in diameter to the second wall diameter 316 allows a gap 318 between the adjustor wall 310a and the circumferential wall 212 of the locator 200. This gap 318 allows for lateral and orbital movement of the adjustor 300 within the locator 200. This movement can allow the magnetic axis 306 to come out of alignment, or be non-coaxial, with the center 204 of the locator 200. The adjustor 300 can be moved laterally, up down, left, and right in relation the position of the locator 200 in FIG. 3D, or can be orbited inside the locator 200 by placing the walls 212, 310a in contact with each other and moving the adjustor 300 while maintaining the contact between the walls 212, 310a. As in the above example, once the actuation motion is removed, the walls 310 can return to the first wall diameter 312 position and the lateral and orbital motions can be prevented and only rotational movement can be allowed.

Figure 4A:
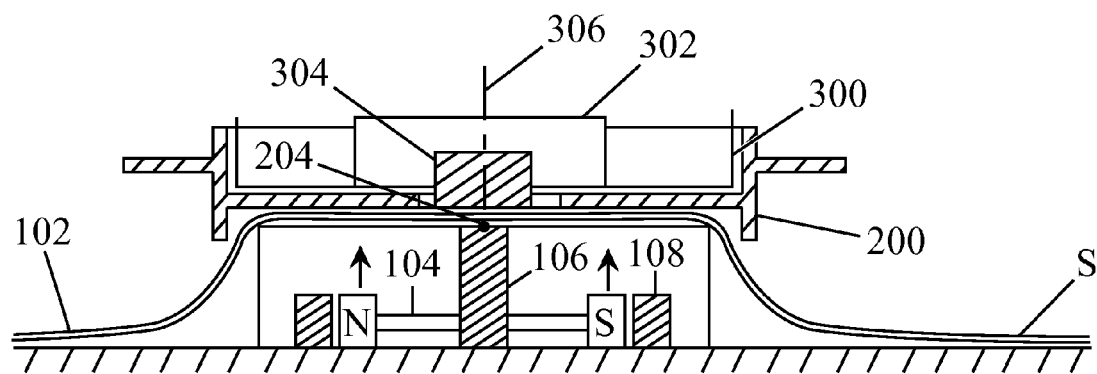
FIG. 4A is a cross-section of the valve, locator and adjustor in alignment.

FIG. 4A illustrates the three elements, the valve 100, the locator 200 and the adjustor 300 in an example. The locator 200 is centered 204 over the rotor axis 106 of the valve. Once the adjustor 300 is placed within the locator 200, the magnetic axis 306 can then be coaxial with the center 204 of the locator 200 and the rotor axis 106 of the valve. In one example, it is only in this position, specifically when the magnetic axis 306 is coaxial with the rotor axis 106, that the magnetic field generated by the magnets 304 is aligned to displace the rotor 104 out of the locking element 108 and into the position to be adjusted. To adjust the position of the rotor 104, the adjustor 300 is rotated within the locator 200 and the magnets 304 move the rotor 104 to the next position. Once the adjustor 300 is removed from the locator 200, the rotor 104 is repositioned into the locked position and restrained by the locking element 108 from any further movement.

Figure 4B:
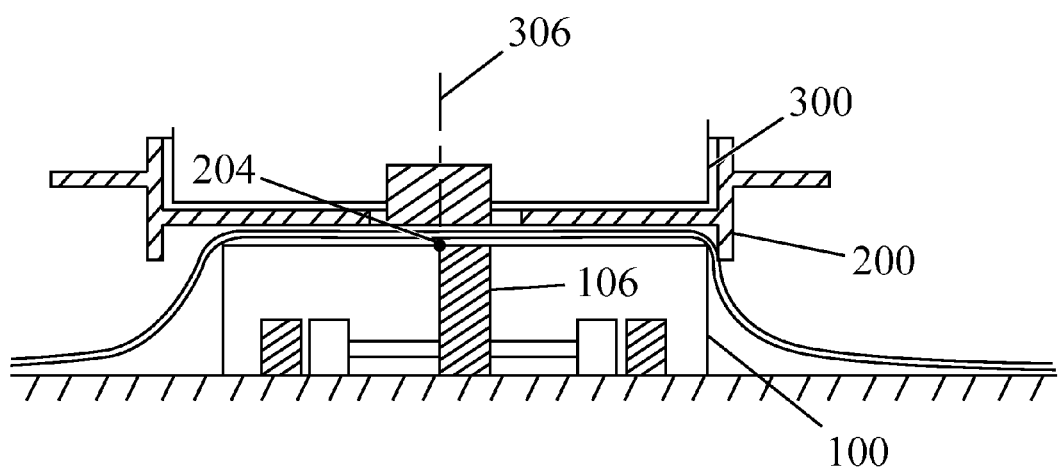
FIG. 4B is a cross-section of the valve, locator and adjustor out of alignment.

The adjustment position described above is typically difficult to achieve on the first attempt by the user. As noted above, at least hair and swelling are reasons why the user misaligns the locator 200 over the valve 100. FIG. 4B illustrates an example of a misalignment. If the center 204 of the locator 200 is not aligned with the rotor axis 106, then it is likely that the magnetic axis 306 is not coaxial with the rotor axis 106 and cannot displace the rotor 104 to permit it to be adjusted. In this situation, multiple attempts are made to position the adjustor 300 to adjust the valve 100. In one example, there is no feedback to the user when the magnetic axis 306 is coaxial with the rotor axis 106, thus the user can easily believe the adjustment has been made. To confirm the adjustment, the user needs a separate tool to determine the position of the rotor 104. An indicator (not illustrated) can be used to determine the position of the rotor 104, and if the indicator reports that the valve 100 has not been adjusted, the user must repeat the process with the locator 200 and adjustor 300, trying to align the magnetic axis 306 with the rotor axis 106 to perform the adjustment.

Allowing the adjustor 300 to move within the locator 200 can, in one example, solve this problem. Setting the wall 310a to the second wall diameter 316 allows the adjustor 300 to move within the locator 200. This allows the magnetic axis 306 to move away from the misaligned center 204 of the locator 200. This increases the chance that the magnetic axis 306 can be moved to a position coaxial with the rotor axis 106 to unlock the rotor 104. In one example, once the rotor 104 is unlocked, moving the adjustor 300 either laterally or orbital within the locator 200 does not allow the rotor 104 to move to the locked position. Thus, the final position of the adjustor 300, once the wall 310 is returned to the first wall diameter 312, does not need to have the magnetic axis 306 coaxial with the rotor axis 106 to perform the adjustment.

Figure 5A:
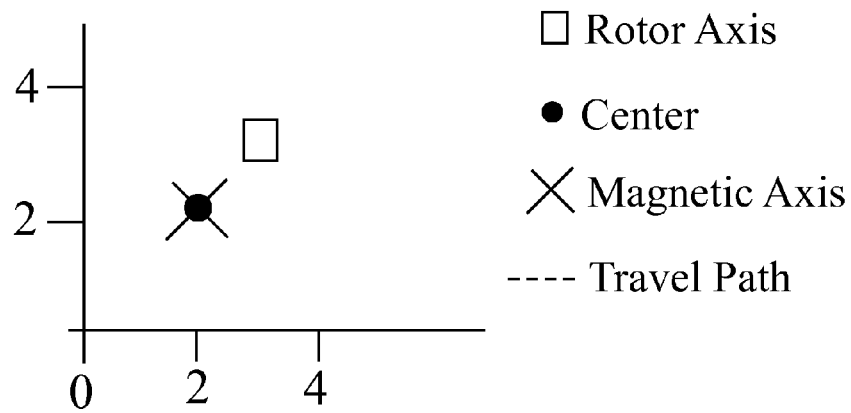
FIGS. 5A-5C are graphs illustrating the position of the rotor axis, center and magnetic axis over time.
Figure 5B:
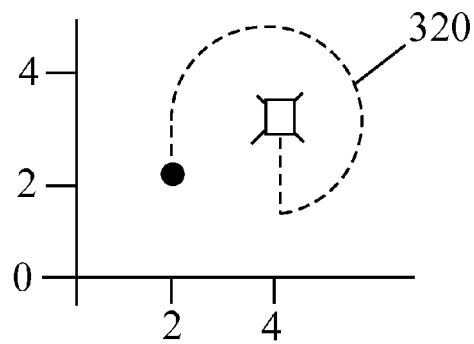
Figure 5C:
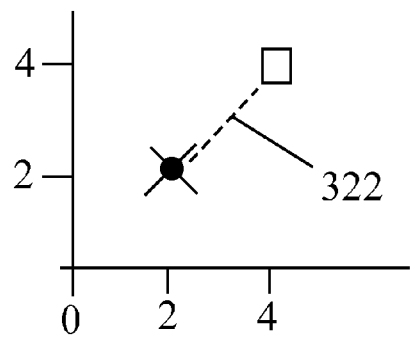

FIGS. 5A-5C illustrate this principal graphically. FIG. 5A is the initial position of the rotor axis 106 in the valve 100, the center 204 of the locator 200 and the magnetic axis 306 of the adjustor 300. The rotor axis 104 is at position (4,4) and the center 204 and the magnetic axis 306 are at position (2,2). Thus, the magnetic axis 306 is not coaxial with the rotor axis 106 and the adjustment of the rotor 104 cannot be performed. FIG. 5B illustrates a position when the user has applied the actuation motion, the wall 310a is in the second wall diameter 316 position, and is moving the adjustor 300 within the locator 200. Line 320 illustrates a possible path the adjustor 300, and thus the magnetic axis 306, can take to result in the magnetic axis 306 being coaxial with the rotor axis 106. Note that the coordinates of the center 204 (2,2) and the rotor axis 106 (4,4) did not change, just the position of the magnetic axis 306 (now (4,4)). Once the two are coaxial, the rotor 104 unlocks, and in FIG. 5C, the magnetic axis 306 can return 322 to its position concentric with the center 204, when the wall 310 is returned to the first wall diameter 312 position. In one example, the adjustor 300 does not provide information to the user that the rotor 104 has been unlocked. It is the motion of the adjustor 300 within the locator 200 that increases the chances that the magnetic axis 306 and the rotor axis 106 align. Since the two did align, the user can now perform the adjustment and the rotor 104 can respond to the adjustor 300. In an example, the rotor 106 only returns to the locked position once the adjustor 300 is removed from the locator 200, the movement of the adjustor 300 within the locator 200 does not lock the rotor 104.

FIG. 6 illustrates a flow chart of an example of this method. A user can palpate the skin 102 to locate the valve 100 (step 400). The user can position the locator 200 over the valve 100 once located (step 402). The position can be such that the rotor axis 106 of the valve 100 and the center 204 of the locator 200 can be either aligned or not aligned. With the locator 200 in place, the user can determine the existing setting of the rotor 104, with, for example, and indicator tool (not illustrated) (step 404). The user then inserts the adjustor 300 in the locator 200 (step 406) and performs the actuation motion (step 408), moving the wall to the second wall diameter 316 position (step 410). The user can then, in this example, move the adjustor 300 in the locator 200 until the magnetic axis 306 is coaxial with the rotor axis 106, unlocking the rotor 104 (step 412). This movement can be called "floating" the adjustor 300 within the locator 200. The magnetic axis 306 is then moved out of alignment with the rotor axis 106 (step 414) and the wall 310 is moved back to the first wall diameter 312 position (step 416). The rotor 104 remains unlocked as the user adjusts the rotor 104 setting with the adjustor (step 418), in one example, by rotating the adjustor 300. The adjustor 300 is then removed from the locator 200 (step 420) locking the rotor 104 into its new setting (step 422). The user then typically confirms the new setting with the indicator tool (step 424).

In a simplified example of the method, FIG. 7 illustrates that the user can position the locator 200 over the valve 100 (step 450) and reduce the size of the adjustor 300 disposed in the locator (step 452). The user can shift the location of the magnetic axis 306 until it is aligned with the rotor axis 106 of the valve, unlocking the rotor 106 for adjustment (step 454). The magnetic axis 306 can be moved out of alignment with the rotor axis 106, but the rotor 104 remains unlocked (step 456). The rotor 104 can be adjusted by rotating the adjustor 300 in the locator 200 (step 458). The rotor 104 can then be locked by removing the adjustor 300 (step 460). In another example, discussed below and illustrated in FIGS. 10A-10D, the adjustor can be recentered within the locator using re-centering elements on the locator (step 457).

Figure 8:
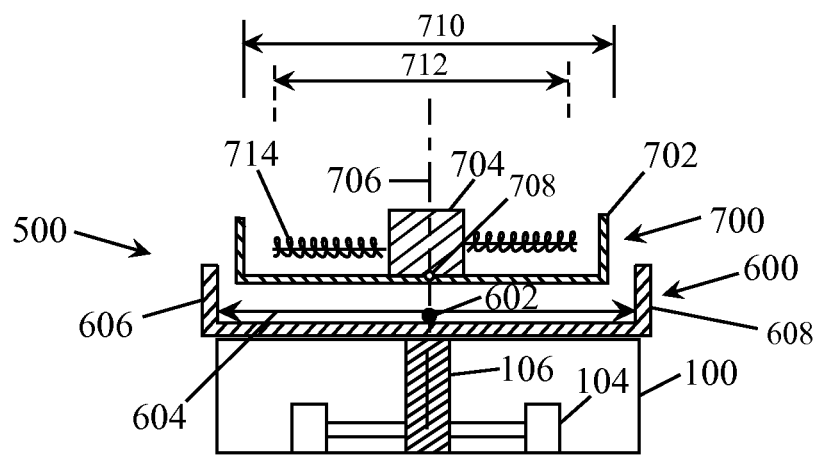
FIG. 8 is a further example of an implanted valve adjustment tool.

FIG. 8 illustrates another example of a tool 500 for changing a current setting of a magnetically readable and settable valve 100 implanted in a living being. The valve 100 has an internal rotor 104 rotatable about a rotor axis 106 having a locked and an unlocked state. The tool includes a locator 600 having a center 602 aligned with the rotor axis 106 when the locator 600 is disposed over the valve 100. In this example, the locator 600 can be a ring and does not have either a bottom or cut-out of the valve. The locator 600 can also have a first dimension 604 approximately perpendicular with the rotor axis 106. The first dimension 604 can be a diameter of the ring 600. A wall 606 of the ring 600 can have a second dimension 606 approximately perpendicular to the first dimension 604. The wall 606 can form a volume in that the ring has a depth to allow an adjustor 700 to be disposed therein.

The adjustor 700 has an adjustable outer wall 702 that fits at least partially within the wall 606 of the ring 600. The adjustor 700 has at least one magnet 704 having a magnetic axis 706. The magnet 704 has a strong enough magnetic field to unlock the internal rotor 104. In one example, the magnet 704 is disposed approximately in a center 708 of the adjustable outer wall 702. The adjustable outer wall 702 has a first position dimension 710 approximately equal to or less than the first dimension 604 of the locator 600. This sizing permits the adjustor 700 to rotate about the center 602 of the locator 600. In an example, the only movement of the adjustor 700 permitted within the ring 600 is rotational about the center 602, accounting for a small amount of play typical between separately formed parts.

The magnetic axis 706 can align with the center 602 of the locator 600 when the adjustor 700 is disposed within and the adjustable outer wall 702 has the first position dimension 710. The adjustable outer wall 702 also has a second position dimension 712 less than the first dimension 604 and less than the first position dimension 710. This sizing permits the adjustor 700 to move more freely inside the ring 600. The adjustor 700 can move at least lateral, rotational, and orbital in the locator 600. This movement can misalign the magnetic axis 706 with the center 602 of the ring 600 when the adjustor 700 is disposed within and the adjustable outer wall 702 has the second position dimension 712. When the magnetic axis 706 aligns with the rotor axis 106, the rotors 104 move into the unlocked state and the rotation of the adjustor 700 sets the valve 100 when unlocked. The rotor 104 can return to the locked state once the adjustor 700 is removed from the locator 600. Once the magnet 704 unlocks the rotor 104, the magnet 704 maintains the rotor 104 in the unlocked state even when the magnetic axis 106 and rotor axis 106 are misaligned.

A plurality of indicators 608 can be disposed on the wall 606 indicating one or more valve settings. In one example, the indicators 608 can be notches or lines on the ring 600.

A flexible element 714 can bias the adjustable outer wall 702 to one of the first position dimension 710 or the second position dimension 712. Thus, the adjustor 700 can be in either position is its static state. The flexible element 714 can be compressed or expanded to allow the adjustable outer wall 702 to move between position dimensions 710, 712. The flexible element 714 can be locked in place or held under force by the user to achieve the non-static position.

All of the above dimension can be diameters.

Figure 9:
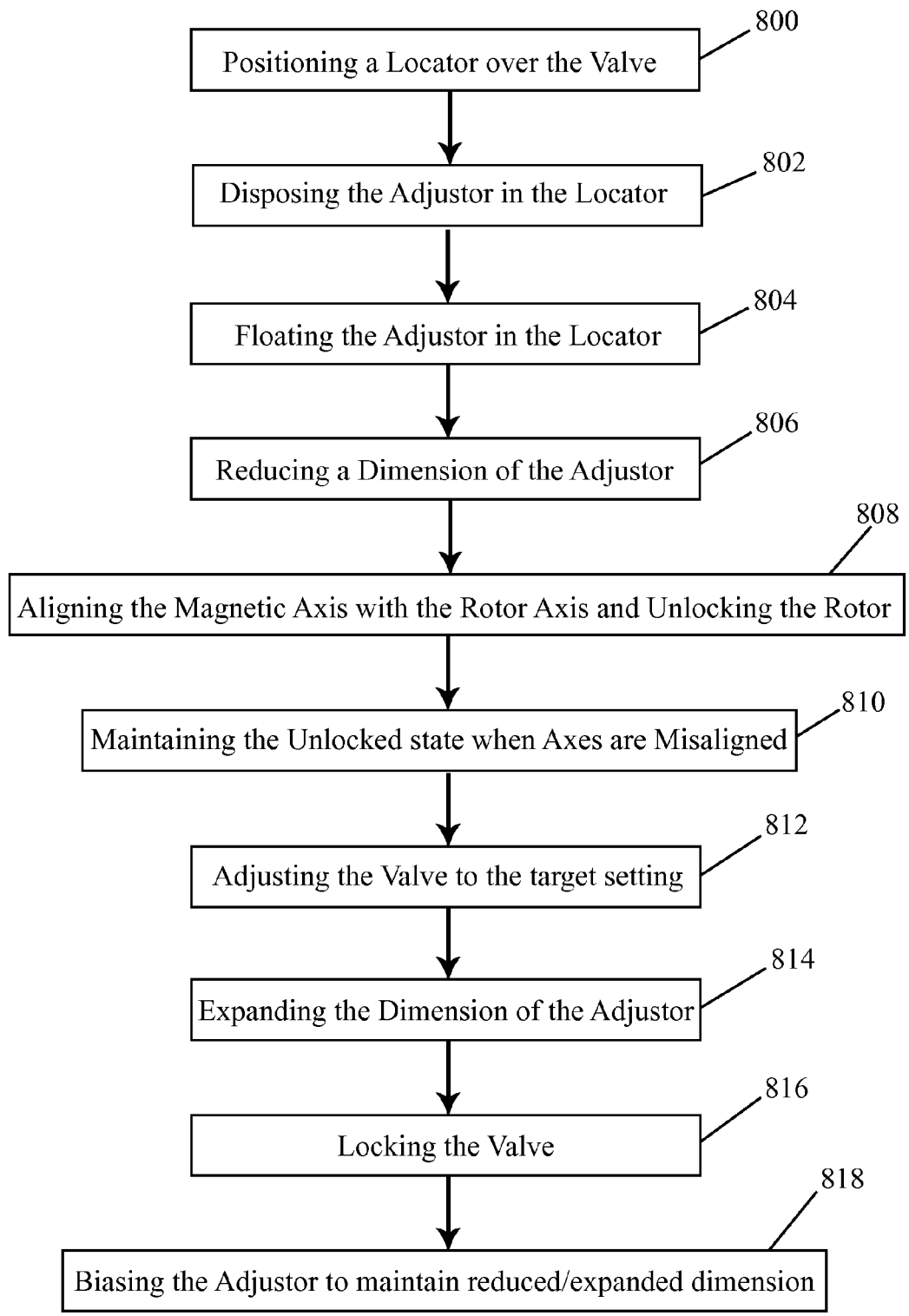
FIG. 9 is flow chart illustrating a further example of a method of adjusting an implanted valve.

FIG. 9 illustrates another example of a method for adjusting the magnetically adjustable valve 100 from a current setting to a target setting. The method includes positioning a locator over the valve (step 800) and disposing the adjustor at least partially within the locator (step 802). Permitting the adjustor to move at least two of lateral, rotational, and orbital in the locator (step 804). This can include the step of reducing a dimension of the adjustor to less than a comparable dimension of the locator (step 806). In other words, reducing the diameter of the adjustor in comparison to the diameter of the locator, this movement allows the adjustor to be non-concentric with the locator. During the movement, aligning the magnetic axis with the rotor axis and displacing the rotor into the unlocked state (step 808). When the magnetic axis and the rotor axis are misaligned, the magnet is still maintaining the unlocked state (step 810). Then, adjust the valve to the target setting (step 812). Adjusting the valve can include expanding the dimension of the adjustor to permit the adjustor to rotate within the locator (step 814). The valve can then be locked again by placing the valve rotor in the locked state by removing the adjustor from the locator (step 816). Further, the adjustor can be biased to maintain one of the reduced dimension or the expanded dimension (step 818).

Figure 10A:
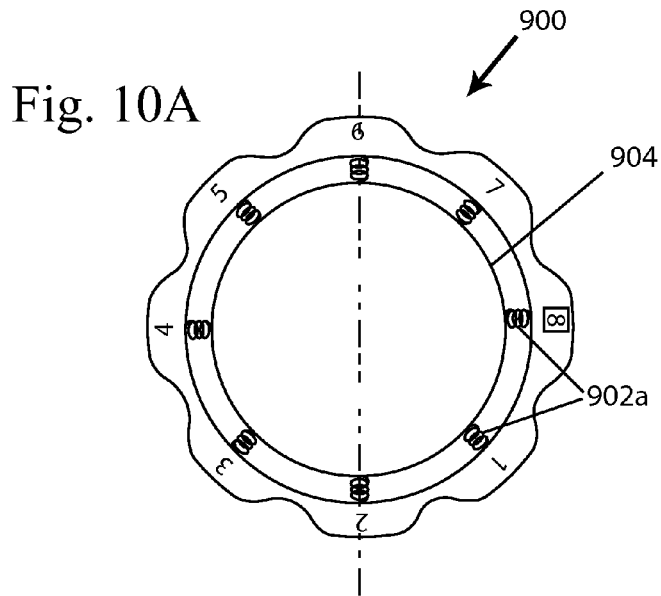
FIGS. 10A and 10C are top views of a locator with various re-centering elements.
Figure 10B:
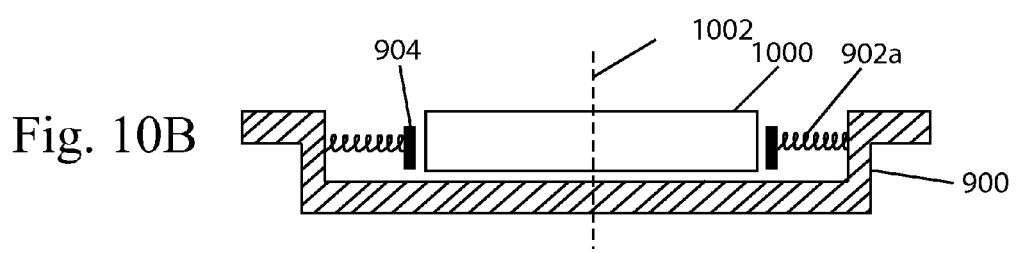
FIGS. 10B and 10D are cross-section views of FIGS. 10A and 10C, respectively.

Other examples of floating an adjustor within a locator are illustrated in FIGS. 10A-10D. In these examples, the locator 900 can include one or more re-centering elements 902. In FIGS. 10A & 10B, the re-centering elements 902 are springs 902a loading a smaller central ring 904. The ring 904 is sized to receive a smaller sized adjustor 1000. Smaller, in this example, can be smaller than a diameter of the adjustor but sized to fit the ring. The smaller diameter can be similar to the second wall diameter 316 noted above. When all springs 902a are balanced, the adjustor 1000, and its magnetic axis 1002, can be centered in the locator 900. However, the springs 902a allow the ring 904, and thus the adjustor 1000 move within the larger locator 900 to assist in aligning the magnetic axis 1002 with the rotor axis.

Figure 10C:
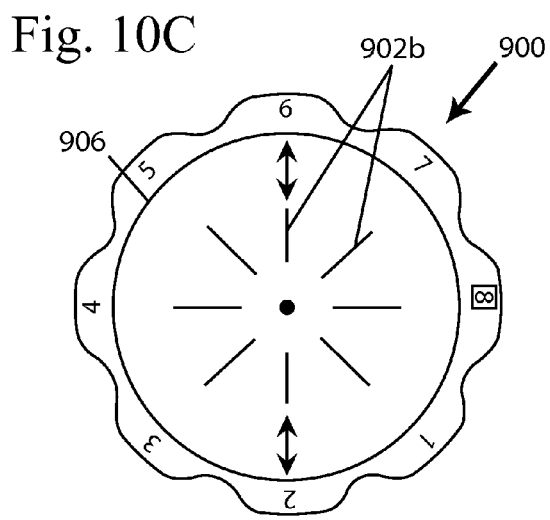
Figure 10D:
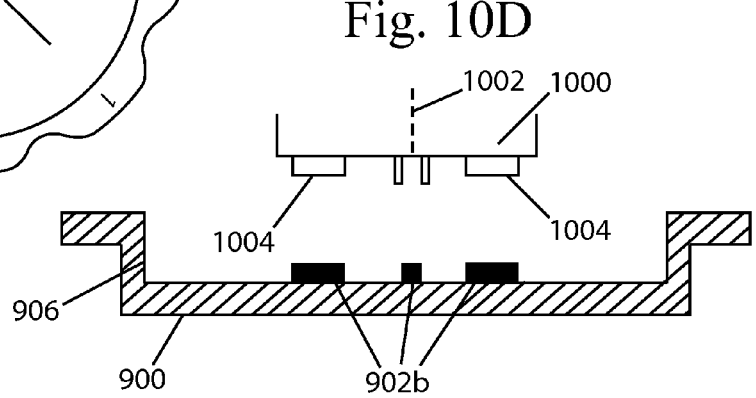

FIGS. 10C & 10D illustrate another example of a locator 900 with re-centering elements 902. In this example, the re-centering elements 902 can be tactile elements 902b. The tactile elements 902b can be a raised or grooved surface of the locator 900. The tactile elements 902b are set inwards from an outer wall 906 of the locator. In one example, the tactile elements 902b are set in a circular pattern and correspond with setting positions of the valve.

Correspondingly, the adjustor 1000 can have a mating tactile surface 1004, grooves or raised surfaces. When the tactile elements 902b and the mating tactile surface 1004 are properly set into each other, and when the user rotates the adjustor 1000 inside of the locator 900, there is some form of physical or auditory feedback to the user. The proper setting to receive feedback is when the adjustor 1000 is centered in the locator 900.

In another example, the physical feedback can also be provided at the time the adjustor 1000 is centered in the locator 900. In either example, when the adjustor 1000 is moving within the locator 900, the user will experience either no or diminished feedback, alerting the user that the adjustor 1000 is not centered. This allows the user to float the adjustor 1000 and then recenter it to adjust the valve.

Further to the above, the tactile elements 902b and the mating tactile surface 1004 can also be inversed, in an example. By that, the feedback delivered to the user can be experienced only when the adjustor 1000 is not centered. Once centered, no feedback is provided to the user.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A tool for changing a current setting of a magnetically readable and settable valve implanted in a living being, the valve having an external cross-section and an internal rotor rotatable about a rotor axis having a locked and an unlocked state, the tool comprising:
   a locator comprising:
      a center aligned with the rotor axis when disposed over the valve;
      a first dimension approximately perpendicular with the rotor axis; and
      a wall having a second dimension approximately perpendicular to the first dimension and forming a volume; and
   an adjustor disposed in the volume, comprising:
      an adjustable outer wall at least partially disposed within the volume; and
      a magnet unlocking the internal rotor, having a magnetic axis, and disposed approximately in a center of the adjustor;
      wherein the adjustable outer wall has a first position dimension approximately equal to or less than the first dimension of the locator, permitting the adjustor to rotate about the center of the locator;
      wherein the magnetic axis is aligned with the center of the locator when the adjustor is disposed in the volume and the adjustable outer wall has the first position dimension;
      wherein the adjustable outer wall has a second position dimension less than the first dimension of the locator and less than the first position dimension, permitting the adjustor to move at least two of lateral, rotational, and orbital in the volume of the locator;
      wherein the magnetic axis can be misaligned with the center of the locator when the adjustor is disposed in the volume and the adjustable outer wall has the second position dimension;
      wherein the rotor is in the unlocked state when the magnetic axis aligns with the rotor axis; and
      wherein the rotation of the adjustor sets the valve when the rotor is in the unlocked state.

2. The tool of claim 1, wherein the locator further comprises:
   a guide to dispose the locator over the valve; and
   a plurality of indicators disposed on the wall indicating one or more valve settings.

3. The tool of claim 1, wherein the rotor returns to the locked state once the adjustor is removed from the volume of the locator.

4. The tool of claim 1, wherein the adjustor further comprises:
   a flexible element biasing the adjustable outer wall to one of the first position dimension or the second position dimension.

5. The tool of claim 4, wherein the flexible element is one of compressed or expanded to allow the adjustable outer wall to move to one of the second position dimension or first position dimension, respectively.

6. The tool of claim 1, wherein once the magnet unlocks the rotor, the magnet maintains the rotor in the unlocked state when the magnetic axis and rotor axis are misaligned.

7. The tool of claim 1, wherein the first dimension, the first position dimension, and the second position dimension are a first diameter, a first position diameter and a second position diameter, respectively.

8. A tool for changing a current setting of a magnetically readable and settable valve implanted in a living being, the valve having an external cross-section and an internal rotor rotatable about a rotor axis having a locked and an unlocked state, the tool comprising:
   a locator comprising:
      a center aligned with the rotor axis when disposed over the valve;
      a first dimension approximately perpendicular with the rotor axis;
      a wall having a second dimension approximately perpendicular to the first dimension and forming a volume; and
      a re-centering element disposed in the volume; and
   an adjustor disposed in the volume, comprising:
      an outer wall at least partially disposed within the volume; and
      a magnet unlocking the internal rotor, having a magnetic axis, and disposed approximately in a center of the adjustor;
      wherein the outer wall has an adjustor dimension less than the first dimension of the locator, permitting the adjustor to move at least two of lateral, rotational, and orbital in the volume of the locator;
      wherein the re-centering element is configured to center the adjustor in the locator, which is the magnetic axis aligned with the center of the locator, permitting the adjustor to rotate about the center of the locator;
      wherein the magnetic axis can be misaligned with the center of the locator when the adjustor is disposed in the volume;
   wherein the rotor is in the unlocked state when the magnetic axis aligns with the rotor axis; and
   wherein the rotation of the adjustor sets the valve when the rotor is in the unlocked state.

9. The tool of claim 8, wherein the re-centering element is one of a resilient element and a ring or one or more tactile elements.

10. A method for adjusting a magnetically adjustable valve from a current setting to a target setting, the valve being implanted in a patient and the valve having an internal rotor rotatable about a rotor axis having a locked state and unlocked state, the method comprising:
   placing a locator over the valve;
   disposing an adjustor having a magnet with a magnetic axis at least partially within the locator;
   permitting the adjustor to move at least two of lateral, rotational, and orbital in the locator;
   aligning the magnetic axis with the rotor axis and displacing the rotor into the unlocked state;
   maintaining the unlocked state when the magnetic axis and the rotor axis are misaligned; and
   adjusting the valve to the target setting.

11. The method of claim 10, further comprising the step of placing the valve rotor in the locked state when removing the adjustor from the locator.

12. The method of claim 10, wherein the permitting step comprises the step of reducing a dimension of the adjustor to less than a comparable dimension of the locator.

13. The method of claim 12, wherein the adjusting step comprises the step of expanding the dimension of the adjustor to permit the adjustor to rotate within the locator.

14. The method of claim 13, further comprising the step of biasing the adjustor to maintain one of the reduced dimension or the expanded dimension.

15. The method of claim 13, further comprising the step of recentering the adjustor within the locator using a re-centering element disposed on the locator.

* * * * *